(12) United States Patent
Sarvazyan et al.

(10) Patent No.: US 8,033,991 B2
(45) Date of Patent: Oct. 11, 2011

(54) HANDGRIP FOR ASSESSMENT OF COLONOSCOPE MANIPULATION

(75) Inventors: Armen P. Sarvazyan, Lambertville, NJ (US); Sergey Tsyuryupa, Westampton, PA (US); Vladimir Egorov, Princeton, NJ (US); Louis Y. Korman, Rockville, MD (US)

(73) Assignee: Artann Laboratories Inc., Trenton, NJ (US)

( * ) Notice: Subject to any disclaimer, the term of this patent is extended or adjusted under 35 U.S.C. 154(b) by 124 days.

(21) Appl. No.: 12/558,737

(22) Filed: Sep. 14, 2009

(65) Prior Publication Data

US 2011/0065991 A1    Mar. 17, 2011

(51) Int. Cl.
*A61B 1/00* (2006.01)
(52) U.S. Cl. .................. 600/131; 600/117; 600/101
(58) Field of Classification Search .......... 600/131, 600/101, 117; 434/262
See application file for complete search history.

(56) References Cited

U.S. PATENT DOCUMENTS

| | | | |
|---|---|---|---|
| 5,623,582 A * | 4/1997 | Rosenberg | 700/264 |
| 6,038,488 A * | 3/2000 | Barnes et al. | 700/161 |
| 6,726,675 B1 * | 4/2004 | Beyar | 604/510 |
| 6,981,945 B1 | 1/2006 | Sarvazyan et al. | |
| 7,526,402 B2 * | 4/2009 | Tanenhaus et al. | 702/151 |
| 2005/0182291 A1 * | 8/2005 | Hirata | 600/101 |
| 2006/0161045 A1 * | 7/2006 | Merril et al. | 600/117 |
| 2008/0146875 A1 * | 6/2008 | Noguchi et al. | 600/117 |
| 2009/0326851 A1 * | 12/2009 | Tanenhaus | 702/96 |

* cited by examiner

*Primary Examiner* — John P Leubecker
(74) *Attorney, Agent, or Firm* — Boris Leschinsky

(57) ABSTRACT

A handgrip for colonoscope shaft is equipped with force, torque, and acceleration sensors allowing for a comprehensive characterization of colonoscope shaft motion, including recognition of obstacles and recording of forces and torques applied at various times during a colonoscopy procedure. An electronic unit is adapted to receive sensors data wirelessly and calculate a variety of motion parameters guiding a medical practitioner during the procedure and aimed at making colonoscopy safer and less painful.

11 Claims, 11 Drawing Sheets

HANDGRIP FOR ASSESSMENT OF COLONOSCOPE MANIPULATION

REFERENCE TO GOVERNMENT-SPONSORED RESEARCH

This invention was made with the U.S. government support under SBIR grant No. R44 DK068936-02 entitled "Colonoscope Force Monitor" and awarded by the National Institute of Health, National Institute of Diabetes and Digestive and Kidney Diseases. The government has certain rights in this invention.

BACKGROUND OF THE INVENTION

The present invention relates generally to devices useful for insertion of steerable catheters and scopes. More particularly, the invention describes a handgrip to be positioned over the shaft of a scope such as a colonoscope allowing measuring and recording of insertion forces coupled with measurements of shaft linear acceleration, same handgrip adapted to measure torque and rotational acceleration about the shaft of the colonoscope, as well as a resulting motion of colonoscope.

In many cases, it has been desirable to examine internal organs, passages and the like of the human body for purposes of diagnosis, biopsy, and therapeutic interventions. One method of examining the internal organs of the patient without major surgery is to insert a remote sensing device such as an endoscope into the body through a natural body orifice such as colon or a specially-prepared surgical opening.

The primary area of application of the invention is for use with a colonoscope but other devices can also be used with the handgrip of the invention. Therefore, the word "colonoscope" is used throughout this description to broadly include various types of direct vision and fiberoptic endoscopes, fiberscopes, arthoscopes, enteroscopes, laparoscopes, and other types or steerable and deflectable catheters, guidewires, cannulaes, and tubes designed to be inserted into blood vessels, tight openings and curved passages.

The use of steerable scopes for internal examination is not limited to medicine. Remote sensing devices can be used to examine the interior of otherwise inaccessible mechanical structures without opening them; such as aircraft wings, the walls of buildings, and the enclosed areas of any structure. In these cases, an internal examination, without putting a major opening in the structure, can help to determine the reason for mechanical failure or the level of corrosion levels.

The preferred area of use for the device of the present invention is in medicine, and more particularly in colonoscopy. Colonoscopy is the preferred method to screen for colorectal cancer, a disease that afflicts 115,000 patients each year in the US. Several million screening, diagnostic and therapeutic colonoscopies are performed each year in the U.S. hospitals and ambulatory surgery centers. Colonoscopy requires a physician to inspect the colonic mucosal surface by applying force to a colonoscope and advancing this flexible tube through a series of stationary and movable colonic loops.

When using a colonoscope, a common problem is to be able to maneuver the inspection end (distal end) of the scope and position it in proximity to the area of interest. This maneuvering is performed by a trained operator who uses a combination of visual inspection of images and tactile coordination to maneuver through the twists and turns found in the colon. The operator subjectively senses the resistance to maneuvers by the "feel" of the instrument and anticipates the amount of force necessary to advance the endoscope shaft forward. The application of force to the colon and its anatomic attachments can be painful. Particularly undesirable is the frequent occurrence of excessive contact pressure on an internal tissue, which can result in pain and in rare cases in colon perforation. Sedation with analgesia is frequently required to make the procedure comfortable. Preliminary studies demonstrate that a significant variation between operators exists in the level of applied push/pull force during examination procedure and that these forces can be excessive. Operator training programs are designed to reduce the variation in technique. However, training metrics remain subjective and the characterization of effective, less forceful insertion methods is not yet available. The need therefore exists to provide a device allowing for an effective, low-cost method to define best practices and to implement these practices as part of medical record keeping, training, ongoing education and quality assurance.

There is an extensive array of surgical instruments, catheters and endoscopes that can be introduced and guided into and through both solid and hollow organ systems such as gastrointestinal tract, blood vessels and heart, urologic and gynecologic systems. These devices are designed to perform a variety of functions such as illumination, spot heating or cooling, introduction of radiographic contrast materials and other fluids, surgical therapies, dilation, etc.

Examples of such guiding or steering techniques and systems for catheters may be found in U.S. Pat. No. 4,983,165 to Loiterman entitled "Guidance System For Vascular Catheter Or The Like," U.S. Pat. No. 4,776,844 to Ueda entitled "Medical Tube," U.S. Pat. No. 4,934,340 to Ebling et al. entitled "Device For Guiding Medical Catheters and Scopes," U.S. Pat. No. 4,930,521 to Metzget et al. entitled"Variable Stiffness Esophageal Catheter," U.S. Pat. No. 3,470 to Barchilon entitled "Dirigible Catheter," U.S. Pat. No. 3,605,725 to Bentov entitled "Controlled Motion Devices," and the Patent Cooperation Treaty ("PCT") Patent Application No. PCT W088/00810 of Tenerz et. al. entitled "Guide For Mechanical Guiding Of A Catheter In Connection With Cardio And Vessel Examination." These catheters, however, fail to give the operator sufficient feedback and control of the distal end of the catheter and make it difficult to manipulate the distal end to achieve a specific isolation of particular desired sections of the body vessel or cavity.

Other steerable catheters or systems have been made to try to give the physician control of the use of the catheter during surgical procedures wherein fluids and the various tools are needed for the operation by providing a flexible tube for controlling the direction of movement of the distal end of the catheter. Examples of these other attempts may be seen in the PCT Patent Application No. W091/11213 of Lundquist et al. entitled "Catheter Steering Mechanism," European Patent Application No. 370,158 of Martin entitled "Catheter For Prolonged Access," and U.S. Pat. No. 4,737,142 to Heckele entitled "Instrument For Examination And Treatment Of Bodily Passages." These devices, however, still fail to provide quantitative characterization of manipulation and control over handling the catheter needed for use with the surgical tools and fluids required for an operation.

One useful design of a handgrip for colonoscope with force and torque measurement capability is described in U.S. Pat. No. 6,981,945 by the same inventors incorporated herein in its entirety by reference. The disclosed handgrip is capable of measuring and presenting to the operator the radial and longitudinal forces applied by the operator during the manipulation with the colonoscope. The handgrip includes an internal sleeve releasably positioned over the shaft of the colonoscope so that it can be disengaged and repositioned by depressing a release button.

The colonoscope manipulations might be characterized not only by applied forces to overcome the tissue resistance but also by acceleration of the endoscope shaft resulting from the applied force. The U.S. Pat. No. 7,526,402 by Tanenhouse entitled "Miniaturized Inertial Measurement Unit and Associated Methods" presents an example of a self-contained, integrated compact measurement unit in which sensors provide measurements of acceleration, linear velocity and angular rate. Increased accuracy is achieved using a noise-reducing algorithm such as wavelet cascade denoising and an error correcting algorithm such as a Kalman filter embedded in a digital signal processor device. In a particular embodiment, two sets of three angle rate sensors are oriented triaxially in opposite directions. Each set is mounted on a different sector of a base oriented normally to the other two and comprising a set of gyroscope. Signals are sent from the angle rate sensors and accelerometer for calculating a change in attitude, position, angular rate, acceleration, and/or velocity of the unit.

Importantly, just measuring force or torque applied to the shaft of colonoscope does not provide a full picture of the procedure. For example, detecting a large force applied to the colonoscope shaft without knowing whether the shaft has moved sufficiently far as a result of such force is insufficient to conclude whether shaft manipulation is proper or not.

The need therefore exists for a colonoscope handgrip able to provide extended set of parameters characterizing colonoscope maneuvering during the examination. This set may include force and torque applied to the endoscope shaft, and resulting linear and rotational accelerations, as well as speed, orientation, and position tracking. The handgrip device of the invention is preferably designed to be easy to use, inexpensive to manufacture and result in less painful and safer colonoscopies.

SUMMARY OF THE INVENTION

Accordingly, it is an object of the present invention to overcome these and other drawbacks of the prior art by providing a novel handgrip for a colonoscope that measures, displays and records various parameters associated with colonoscope maneuvering during a colonoscopy procedure. These parameters may include force and torque applied to endoscope shaft, its linear and rotational accelerations, as well as speed, orientation, and position tracking of the handgrip.

It is another object of the invention to provide a handgrip for a colonoscope adapted to measure both the linear force applied to the shaft as well as its linear acceleration allowing to measure response to such force from the movement of the colonoscope inside the patient.

It is a further object of the invention to provide a handgrip for a colonoscope adapted to measure both the torque applied to the shaft as well as its rotational acceleration allowing measuring response to such applied torque from the rotation of the colonoscope inside the patient.

It is another object of the present invention to provide a handgrip for assessment of colonoscope manipulation, which can be easily used with a variety of commercially available colonoscope instruments.

It is a further object of the present invention to provide a handgrip adapted for releasably disengaging and sliding along the shaft of the colonoscope during its insertion and removal so that the area of grip by the hand of the operator can be changed depending on the clinical necessity.

It is yet a further object of the present invention to provide a handgrip, which can be reused multiple times and can withstand disinfection and sterilization by all commonly used methods without the loss of sensitivity of any of its measuring parameters.

The handgrip of the invention consists of an internal sleeve and an external sleeve positioned around the internal sleeve. An engaging means is positioned between both sleeves. As a result of that arrangement, in order to manipulate the colonoscope shaft, the operator has to apply the necessary force and torque to the external sleeve of the device, which then transmits that force and torque through the engaging means first to the internal sleeve and then further to the colonoscope shaft itself. Various sensors are incorporated with the engaging means so that operator's manipulations of the external sleeve can be accurately measured and recorded. Colonoscope manipulation data acquired from the sensors are then transmitted to a control unit such as for example a personal computer or a hospital electronic data storage system and can be displayed or stored after an appropriate data processing.

In order to place the handgrip of the invention over the shaft of the colonoscope, provisions are made to allow both sleeves to be opened and closed such as with a clam-shell design. Alternatively, the colonoscope shaft can be passed through the opening in a single-body handgrip prior to the procedure and removed thereafter.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

Figure 1:
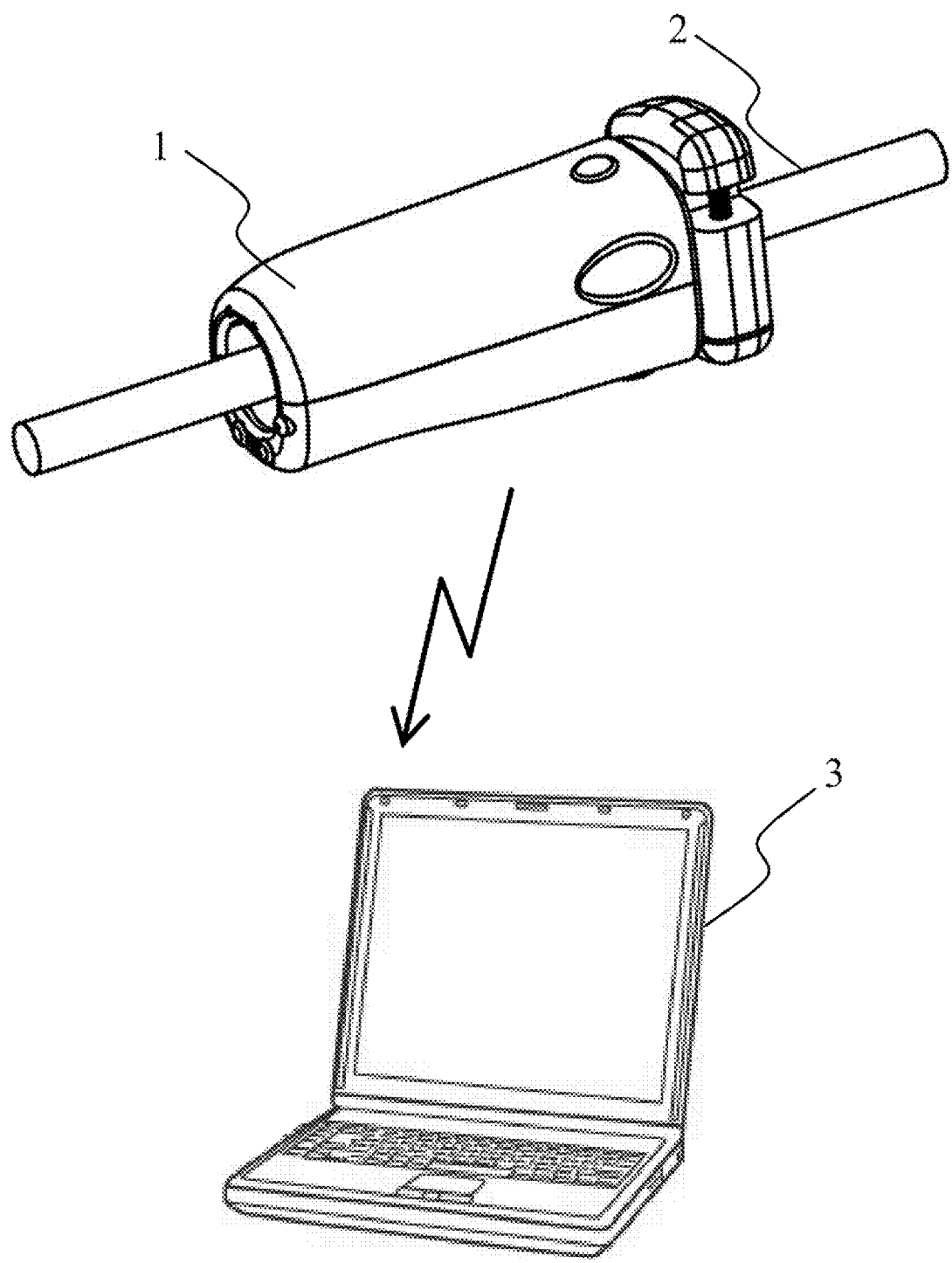
FIG. 1 is a general outline of the system of the invention including a colonoscope handgrip and data processing means.

Colonoscopy procedure will now be briefly described. Colonoscopy requires that push, pull and torque forces be applied to the endoscope shaft to advance it through the colon. The applied forces account for the two most important limitations of colonoscopy: pain and colonic perforation. Conscious and deep sedation is used to control pain and the anxiety associated with anticipation of pain. This sedation is administered as a combination of an analgesic and a sedative medication. Sedation enables the patient to tolerate greater forces applied by the operator to advance the instrument. There is significant variability between operators in the amount of sedation used. While some operators use little or no sedation, others use deep sedation. These observations suggest that the technical manipulation of the colonoscope is critically important in causing pain. In addition, perforation is a rare but most serious complication of colonoscopy. The reported rate of colonic perforations varies widely and is estimated to be 0.01% to 0.3%. Perforations occur in both diagnostic and therapeutic procedures.

The structure, position and relation of the colon to the peritoneum and other organs affect the performance of the colonoscopy. Specific factors influencing the success of the procedure include: redundancy of colonic loops, presence of adhesions, prior surgery, acute angulation and stenosis with or without diverticular disease. The colon contains a number of loops in a variety of configurations and the force applied to the colonoscope may result in forward motion or a lateral force that is often associated with pain. Prior surgery frequently restricts colon mobility and increases the force required to traverse its particular affected part. Acute angulations are found in the recto-sigmoid, splenic and hepatic flexures and require the operator to increase push/pull and torque force to advance the instrument. The application of force against the wall of the colon can be substantial. Finally, colon stenosis or narrowing can be encountered—this often restricts the colon mobility and adds to the difficulties posed by angulation and other distortions of colonic configuration. In general, patient discomfort is considered to be a result of the force applied to the colonoscope. Increases in pain are likely to represent excessive force.

Importantly, knowing only force or torque applied to the shaft of colonoscope is not sufficient to describe the procedure accurately. For example, detection of a certain level of push force along with an appropriate advancement of colonoscope shaft indicates a proper course of colonoscopy. At the same time, detection of the same force without any corresponding motion of colonoscope shaft indicates encountering an obstacle inside the colon and possibly resulting in patient's discomfort or pain. Therefore, a comprehensive characterization of the procedure is only possible by knowing the applied force and torque together with a resulting motion of the colonoscope shaft. The present invention is aimed to provide for such a comprehensive characterization as described below.

A detailed description of the present invention now follows with reference to accompanying drawings in which like elements are indicated by like reference letters and numerals.

A device general view is shown in FIG. 1. The handgrip 1 is shown placed around shaft 2 of the colonoscope. Note that only a small portion of the shaft is shown on the drawing in the vicinity of the grip area for the operator to handle the device. The handgrip is equipped with force, torque and acceleration sensors as will be described in more detail below. In the first configuration shown in FIG. 1, the data from the handgrip sensors are transmitted wirelessly to computer 3 for data processing and recording. This transmission can be done using any number of known wireless protocols such as Bluetooth for example. As can be well appreciated by those skilled in the art, the wired transmission of data from the handgrip to the computer is also possible and will fall within the scope of the invention. The wireless handgrip has an advantage of providing maximal manipulation freedom for the operator.

In the second configuration (not shown on the drawings), the data from the handgrip sensors are sent directly to the colonoscope image display apparatus. These data are envisioned to be incorporated on the colonoscope display being integrated together with real time colonoscope camera view to provide a quantitative measure of applied forces and dynamic response of the tissue. This configuration is especially beneficial for integrated devices when the handgrip of the invention is a part of the entire colonoscope setup.

Figure 2:
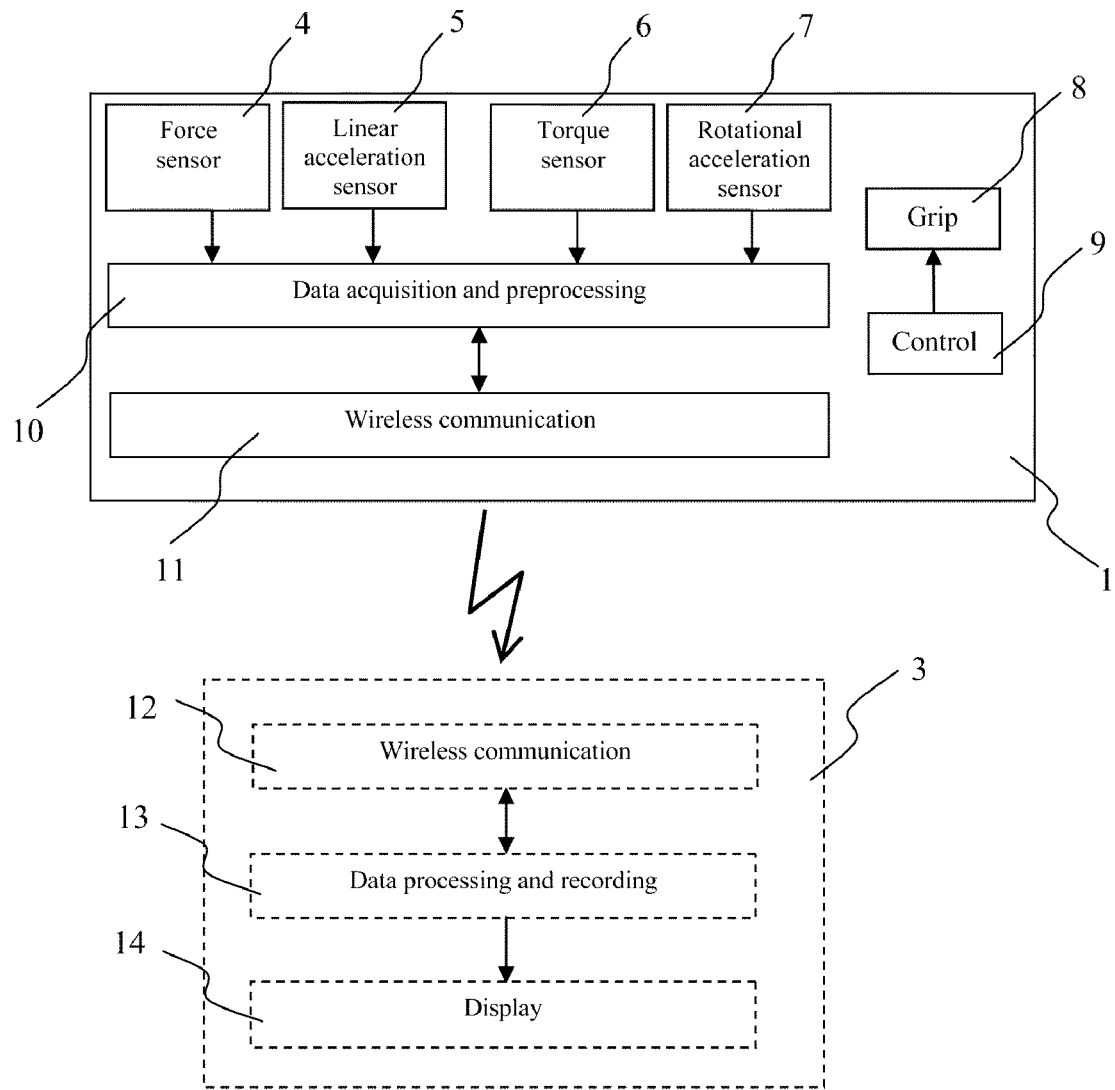
FIG. 2 is device block diagram.

The block diagram of the handgrip is shown on the FIG. 2. The force sensor 4 and torque sensor 6 adapted to respectively measure the force and torque applied to endoscope shaft. Linear acceleration data is provided by sensor 5 and rotational acceleration data is provided by sensor 7. Together these sensors allow characterization of both applied forces and resulting motions of the colonoscope shaft. The data processing unit 10 is employed for data acquisition and preprocessing. The handgrip wireless communication module 11 provides data transmission to the electronic unit through wireless communication means 12 for further data processing and recording/storing in module 13. The results are displayed on the indicator 14. A handgrip manipulation is accompanied by colonoscope intercept. The grip system 8 provides engage and release function of the colonoscope shaft as controlled by commands of the control unit 9 in accordance with a stored processing algorithm.

The linear and rotational acceleration sensors 5 and 7 might be composed of a combination of accelerometers, magnetometers, and gyroscopes (linear and rotational). The purpose of the linear acceleration sensor 5 is to measure linear acceleration of handgrip motion along the handgrip central axis. The purpose of the sensor 7 is to measure rotational acceleration of the handgrip around its central axis. The direction of the linear acceleration is parallel with the direction of linear force applied to the endoscope shaft which is measured by a force sensor 4. The direction of rotational acceleration coincides with applied torque which is measured by the torque sensor 6.

The linear and rotational accelerations can be acquired directly from or calculated from the acquired signals of sensor 5 and 7 using different approaches. One of the possible solutions for calculation of the linear acceleration may comprise the steps of:
  a) measuring elevation, rotation, and azimuth angles of the handgrip 1 relative to the gravity and magnetic vectors of the Earth,
  b) measuring 3-D acceleration vector by a 3-axis acceleration sensor,
  c) calculating 3-D acceleration vector produced by only displacement of the handgrip by means of subtraction of gravity vector from the 3-D acceleration vector of step (b), and
  d) calculating a projection of the 3-D acceleration vector calculated in step (c) to the central axis of the handgrip 1.

One of the possible solutions for calculating the rotational acceleration may comprise the steps of:
  a) measuring elevation, rotation and azimuth angles of the handgrip 1 relative to the gravity vector of the Earth,
  b) measuring 3-D rotational accelerations by rotational gyroscopes, and
  c) calculating the rotational acceleration around the central axis from 3-D rotational accelerations taking into account the contribution of the gravity vector of the Earth.

Importantly, knowing both linear force and linear acceleration allows a more comprehensive characterization of the endoscope shaft push/pull manipulations, and knowing both torque and rotational acceleration allows an extended characterization of the endoscope rotational manipulations. These data allow recognition of an encountered obstacle and characterizing the way in which a medical practitioner moves the shaft of the endoscope to overcome the obstacle and advance the device forward. Such obstacle may be an obstruction or a turn in the colon anatomy. A ratio of force to linear acceleration characterizes a tissue resistance to pull/push motions. A ratio of torque to rotational acceleration characterizes a rotational friction between the endoscope and tissue.

Additionally, the acceleration data of sensors 5 and 7 can be used for calculating a speed of the handgrip motion as well as the changes in the endoscope positioning during the endoscope manipulation.

Figure 3:
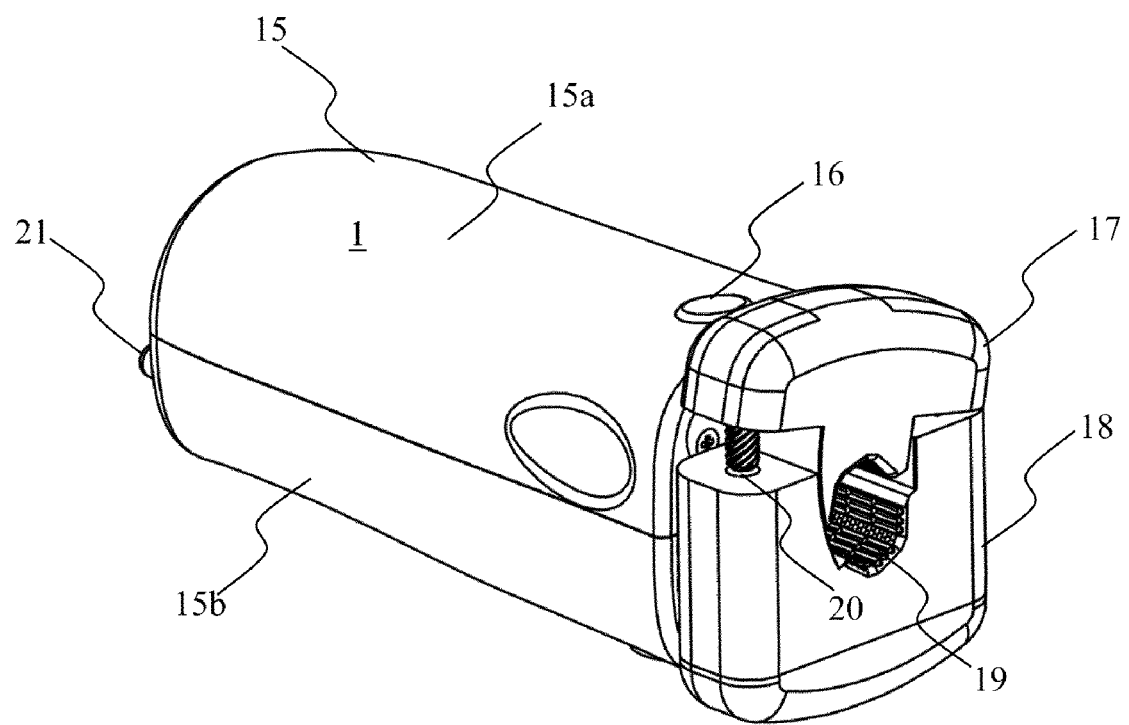
FIG. 3 is a view of the handgrip assembly.
Figure 4:
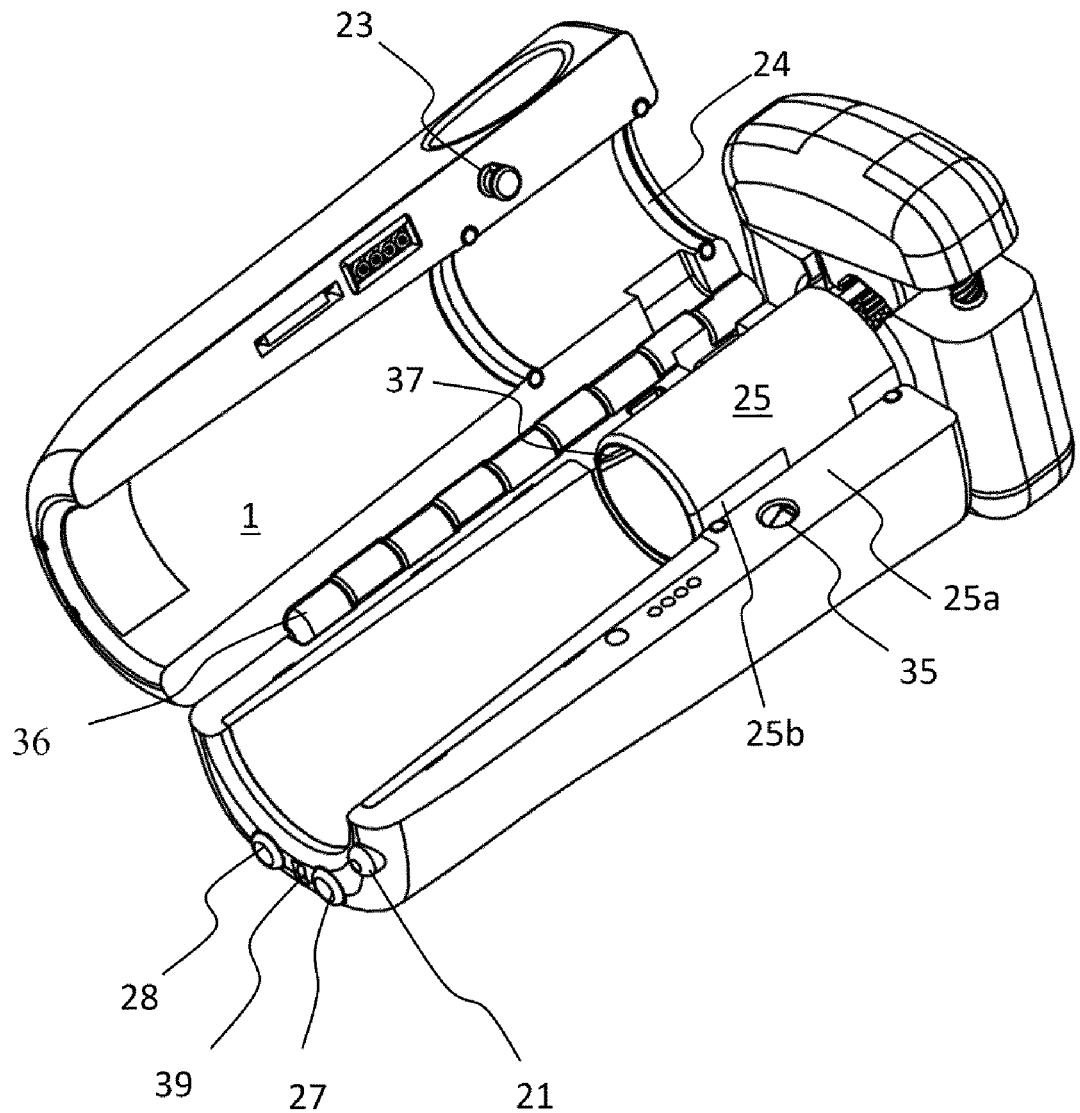
FIG. 4 is a view of the same but with the external sleeve opened.

The internal design of the handgrip 1 of the invention will now be described in more detail. The embodiment of the handgrip 1 is shown in greater detail in FIGS. 3-11. The handgrip 1 consists of an external sleeve 15 positioned over an internal sleeve 25. The internal sleeve 25 smoothly rotates inside the external sleeve 15 aided by bearings 24 placed on the inner diameter of the external sleeve 15 (see FIG. 4). These bearings 24 may be made as Teflon® rings. The external sleeve 15 is sized and shaped externally for an easy grip by a human hand as shown in FIG. 3. In its preferred configuration, the length of the external sleeve 15 is such that it covers entirely the internal sleeve 25 so that the operator holds the entire handgrip 1 only by its external sleeve 25. To allow placement of handgrip 1 over shaft 2 of the colonoscope, the external sleeve 15 can be split in two halves 15a and 15b connected together on one side by a continuous optionally spring-loaded hinge 36 so as to allow them to open when the clamp 23 is released. Button 21 releases the spring-loaded grip 35 of the clamp 23 so that the two external sleeve halves 15a and 15b can be swung open along the hinge 36 (see FIG. 4). Other methods on connecting two halves are also contemplated within the scope of the invention such as sliding of one half along another, completely disengaging of one half from another, etc.

Figure 6:
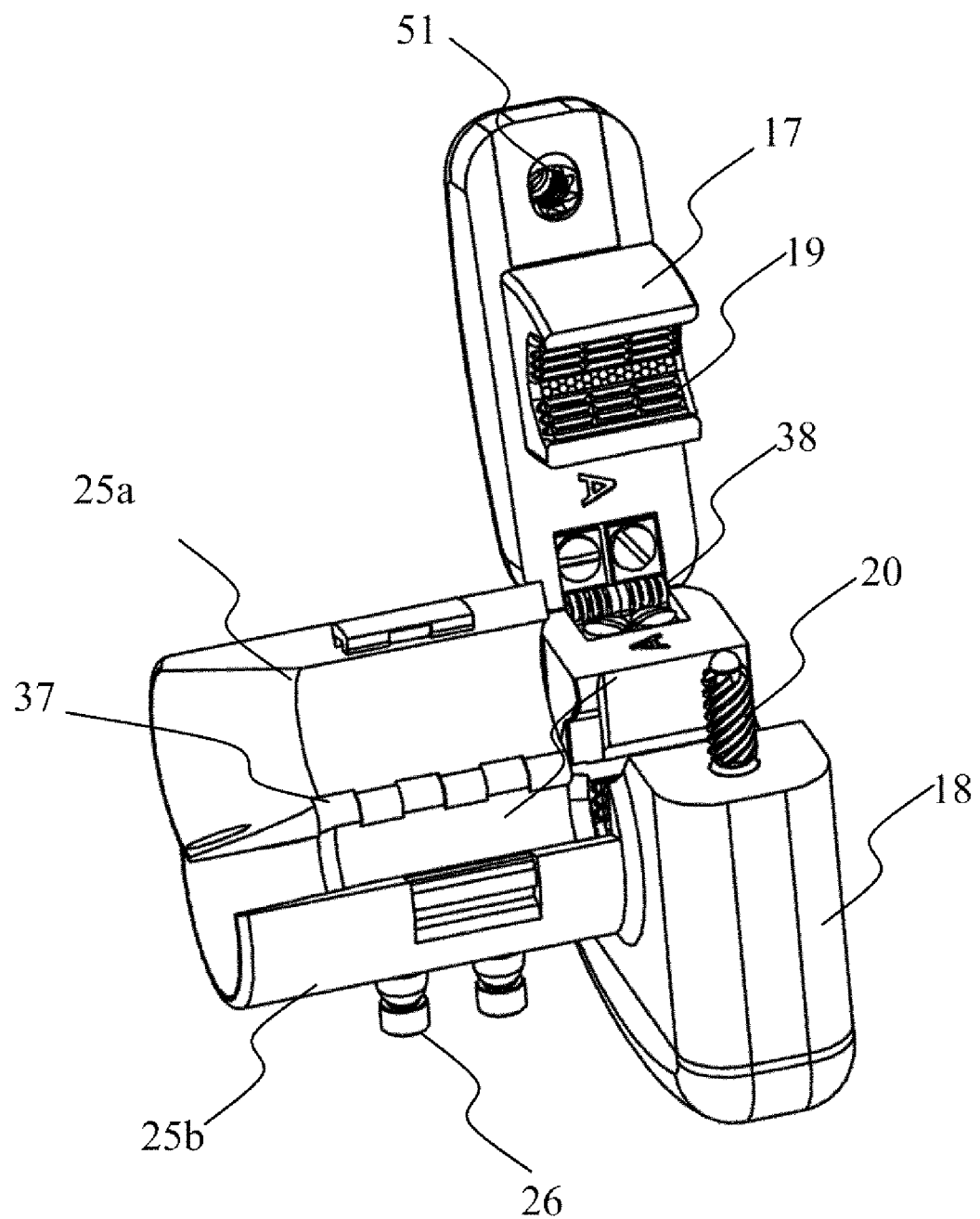
FIG. 6 is a view of internal sleeve combined with grip in its opened position.

The internal sleeve 25 in turn also consists of two halves 25a and 25b connected together at one side by a hinge 37 (see FIG. 6). The two pieces releasably snap together on the other side from the hinge. The shape of the sleeves is such that they fit entirely inside the external sleeve 15. The internal sleeve 25 may therefore be positioned over the colonoscope shaft and engaged therewith.

Release button 16 is incorporated on the outside of the external sleeve 15 (see FIG. 3) so that the handgrip 1 can be slidingly released from the shaft 2 of the colonoscope allowing its relocating to a new position. When not pressed, the release button 16 is designed to have the movable part 17 of the shaft grip to continuously engage shaft 2 with a rough surface 19. This can be generally referred to as a "normally closed" position, meaning a position in which the device is continuously engaged with the shaft of the colonoscope unless the release button 16 is depressed. Pressing the release button 16 activates a motor to loosen the screw 20 by a turning it a few revolutions only causing the movable grip part 17 of the grip assembly 18 to slightly lift off the shaft 2. With the grip part 17 so raised, the handgrip 1 can be moved along the colonoscope shaft 2. When the button 16 is released, the screw 20 is turned the other way causing tightening of the screw 20 and lowering of the movable grip part 17, which again engages the shaft 2 and firmly holds the handgrip 1 on the colonoscope in its new position.

When button 27 is held down continuously, the screw 20 is turned continuously until the movable part 17 is free to open along the hinge 38. The entire handgrip can then be either placed initially onto the shaft 2 or removed from the shaft 2 at the end of the procedure. While this example describes a screw-activated engaging system to fix the handgrip 1 on the colonoscope shaft 2, other engaging and disengaging designs that provide the same grip and release of the colonoscope are contemplated within the scope of this invention. Button 28 is the power on/off button (see FIG. 4). User communication indicator 39 provides device performance information to the user, for example using blinking lights or a screen displaying text or other means of informing the user.

Figure 5:
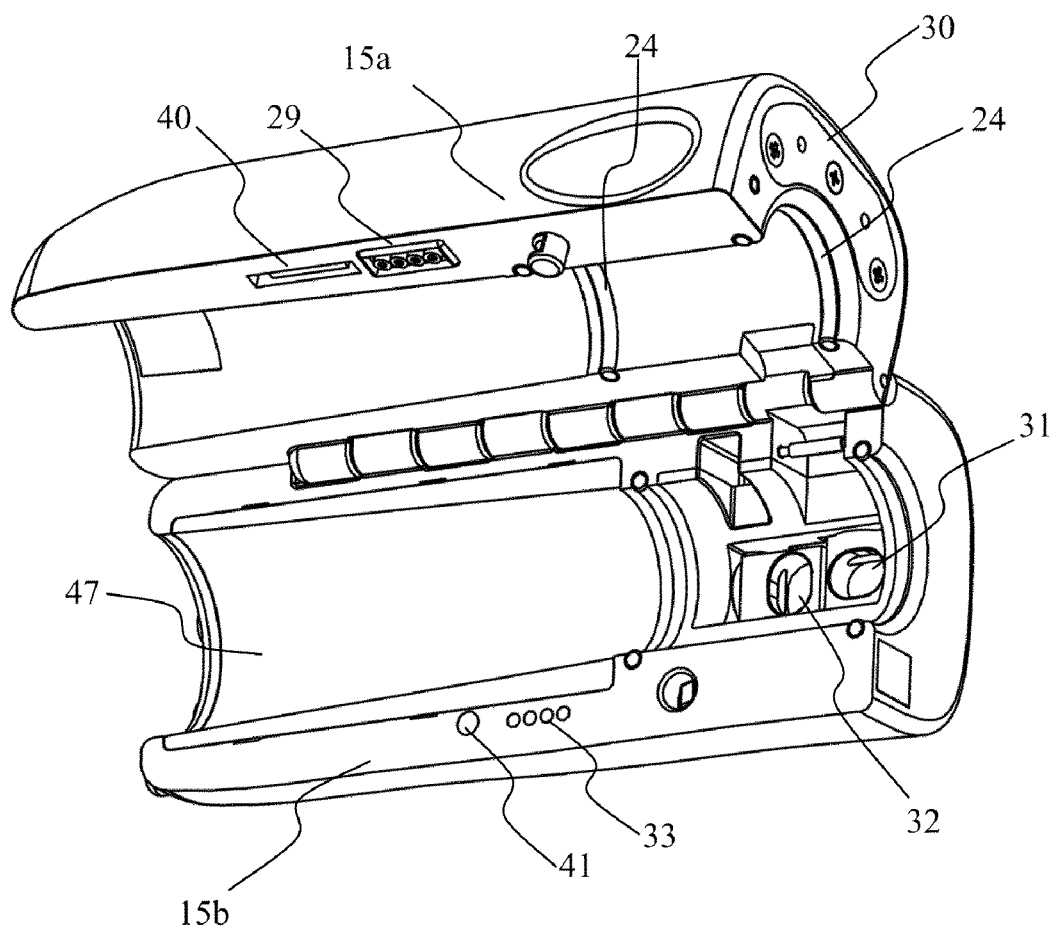
FIG. 5 is a view of just the external sleeve in its opened position.

FIG. 5 illustrates the external sleeve 15 opened along the spring-loaded hinge 36 with the inner sleeve 25 removed. The top external sleeve half 15a houses the batteries inside the battery compartment covered with a door 30. The power is transmitted to the bottom external sleeve 15b by spring-loaded movable pin contacts 29 and fixed pin contacts 33. While this one design approach of transferring the power between the two halves is illustrated on the drawing, this invention anticipates other designs that could be used including but not limited to wires through the hinge, or other modular contact methods. To remove live voltage from the contacts 29 when the two halves 15a and 15b are open, an optional relay 40 and magnet 41 can be used. Housed on the bottom external sleeve 15b is the force sensor system 32 and the torque sensor system 31 which are better seen in FIG. 7B and FIG. 8.

FIG. 6 shows the details of the internal sleeve 25 combined with grip 18. Ball bearings 26 are placed into sensor slot. They work to minimize cross-talk between the force and torque sensors. The internal sleeve halves 25a, 25b and movable portion 17 of shaft grip are in the open position here to show possibility of easy loading onto a colonoscope shaft 2. Lead screw 20 and lead nut 51 provide for fast grip and release of the colonoscope shaft.

Figure 7A:
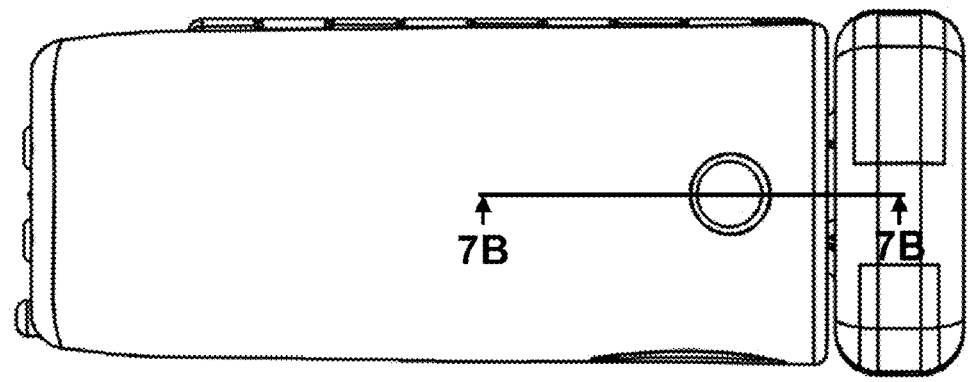
FIG. 7A is a top view of the device.
Figure 7B:
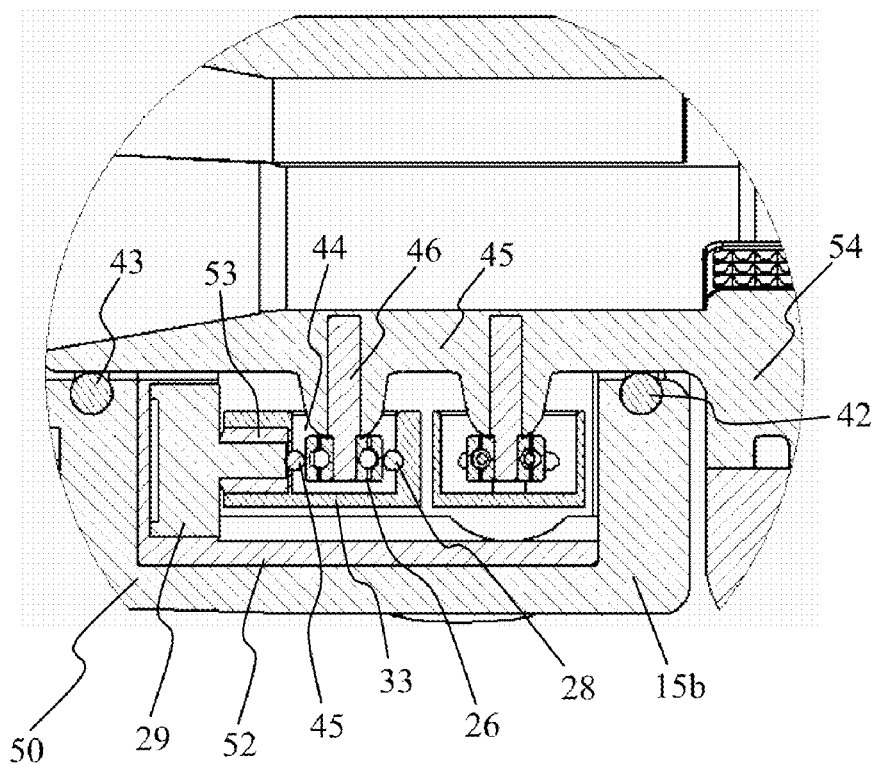
FIG. 7B is partial cross-sectional view of the engaging means and sensors as shown in FIG. 7A, FIGS. 8A and 8B are views of the force sensors module.
Figure 8A:
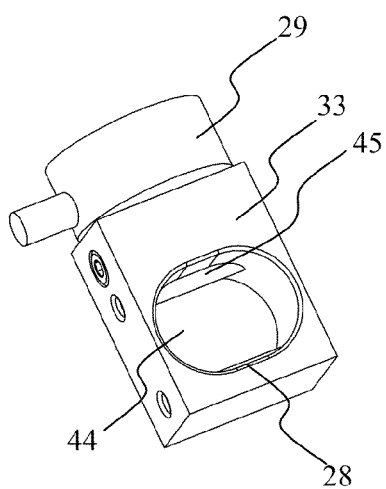
Figure 8B:
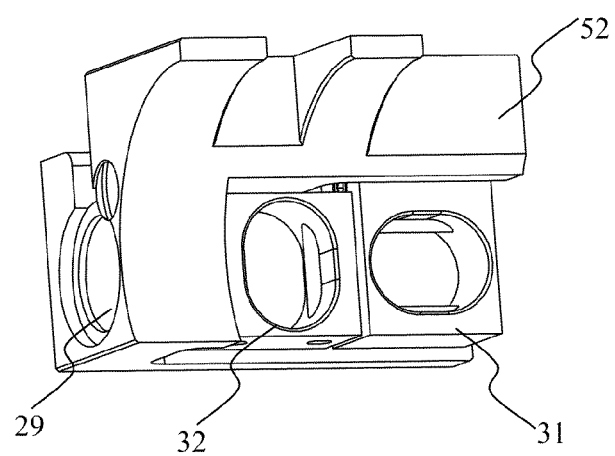

FIG. 7B shows a cross-sectional view along the central axis of the handgrip. It shows a portion 45 of the inner sleeve 25 resting on Teflon bearings 42 and 43 of the portion 50 of the external sleeve 15b. Force sensor 32 and torque sensor 31 mounted in the housings 33 have identical designs. The difference between the sensors is only their orientation—force and torque sensors are installed orthogonally to each other in the sensors holder 52, which in turn is placed inside the external sleeve 50. The force sensor 32 is oriented along the central axis of the handgrip while the torque sensor 31 is oriented perpendicular thereto. The force sensor 32 with its housing 33 is shown separately in the FIG. 8A, while the entire force and torque sensor module is shown in FIG. 8B.

A cross-sectional view of a force sensor is seen in FIG. 7B. It includes a load cell 29 oriented along the force sensor sensitivity axis, which is parallel to the linear axis of the handgrip and colonoscope shaft 2. To the left of the load cell 29 there is shown the housing 33 attached to the load cell 29 through an adapter ring 53. The housing 33 has a slot 44 with round rods 28 and 45 shown in cross-section in FIG. 7B. The middle points of rods 28 and 45 are aligned with the central axis of the load cell 29. Pin 46 extends from the internal sleeve 15 into the space of slot 44. It contains a ball bearing 26 on its bottom end. The ball bearing 26 is sized to be trapped between rods 45 and 28. When a push force is applied to the handgrip, the external sleeve 50 presses the ball bearing 26 against the rod 45, causing housing 33 to apply force through adapter ring 53 to the load cell 29 (where it is measured) and then to the internal sleeve 54. The push force is therefore applied from the handgrip through the external sleeve to the internal sleeve and ultimately to the gripped colonoscope shaft.

Similarly, a pull force applied to the external sleeve 50 presses the ball bearing 26 against the rod 28, so housing 33 applies the force through the load cell 29 (straining the force sensor and measuring pull force) to the internal sleeve 54. The slot 44 is shaped to have extra space on both sides of the pin 46 as shown in FIG. 8A, so the ball bearing 26 transfers only the pull/push force without disturbance caused by rotation of the handgrip. Rotation motion causes the ball bearing 26 to slide along rods 45 and 28 into one of the extra spaces of the slot 44.

The torque sensor 31 works in the same fashion, but due to its radial orientation its load cell measures only rotational push and pull forces. To achieve that objective, the sensitivity direction of the torque sensor is oriented perpendicular to the central axis of the handgrip and parallel to the direction of endoscope shaft rotation.

Figure 9:
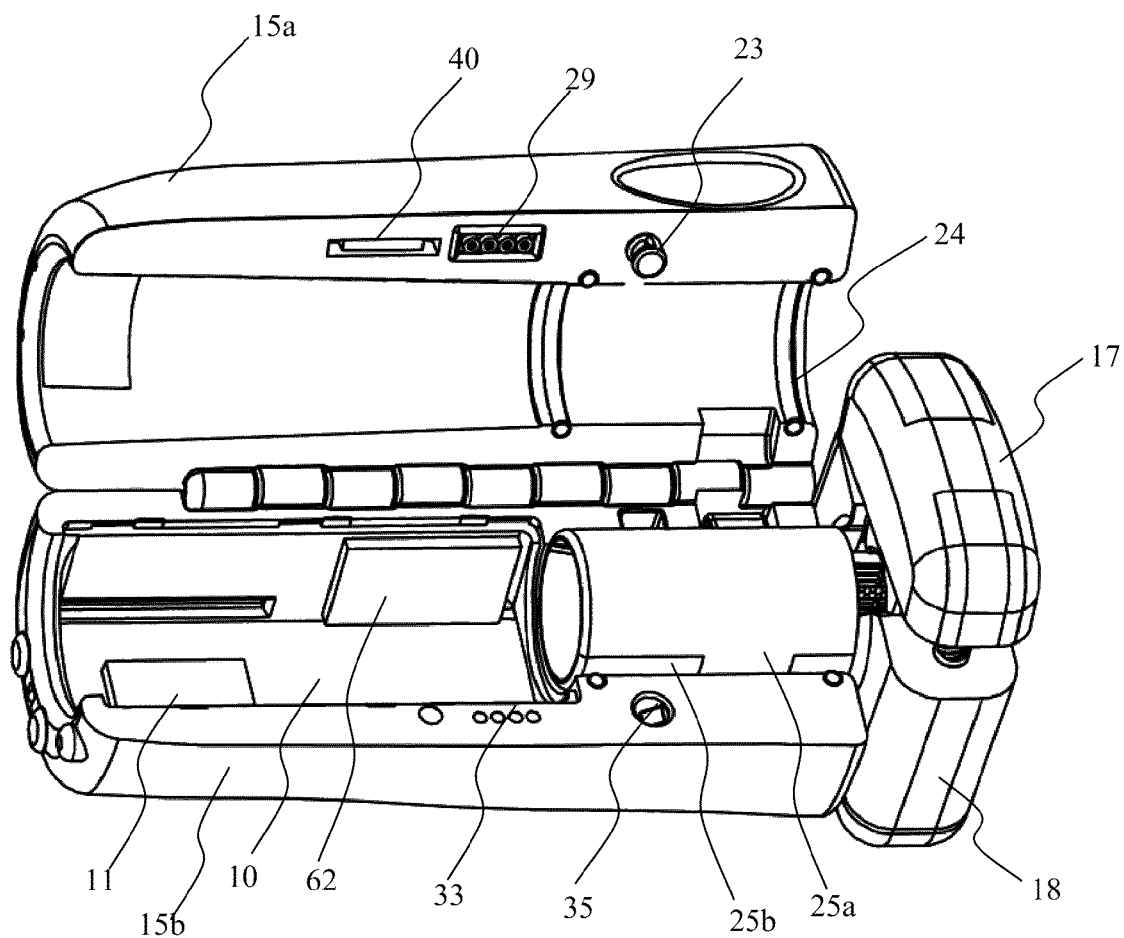
FIG. 9 is a view of FIG. 3 but with electronic cover opened.

FIG. 9 displays the handgrip 1 of the invention having external sleeves 15a and 15b opened along the hinge 36. The electronics compartment cover 47 (as seen in FIG. 5) is removed to expose an acceleration sensor assembly 62 which includes linear and rotational acceleration sensors. The acceleration sensor assembly 62 may include a combination of accelerometers, magnetometers, and gyroscope sensors. One example of such acceleration sensor assembly is InertiaCube3 manufactured by InterSense Inc. (Bedford, Mass.). It includes 3-axis accelerometer, 3-axis magnetometer, and 3-axis gyroscope sensor.

The mounting of the linear acceleration sensor inside the handgrip 1 is done in a way as to align the sensitivity axis of linear acceleration sensor with the central axis of the handgrip 1 and therefore of the colonoscope shaft 2. One purpose of the acceleration sensor assembly 62 is to measure acceleration of handgrip motion along the handgrip central axis and rotational acceleration of the endoscope shaft around its axis. Due to above mentioned mounting of the linear acceleration sensor, the direction of measured acceleration is parallel with the direction of linear force applied to the endoscope shaft, which is measured by the force sensor. At the same time, the direction of measured rotational acceleration coincides with applied torque which is measured by the torque sensor. The sensor signals from of the acceleration sensor assembly 62 are sent to the electronic board 10, which also receives data from the force sensor system 32 and torque sensor system 31 shown in FIGS. 8A and 8B. After preprocessing the data from force, torque and acceleration sensors are wirelessly transmitted by data transmission means to the computer 3 for processing, displaying, storage, and analysis. The data processing includes transformation of sensor signals into force and acceleration values using the stored sensor calibration data.

Figure 10:
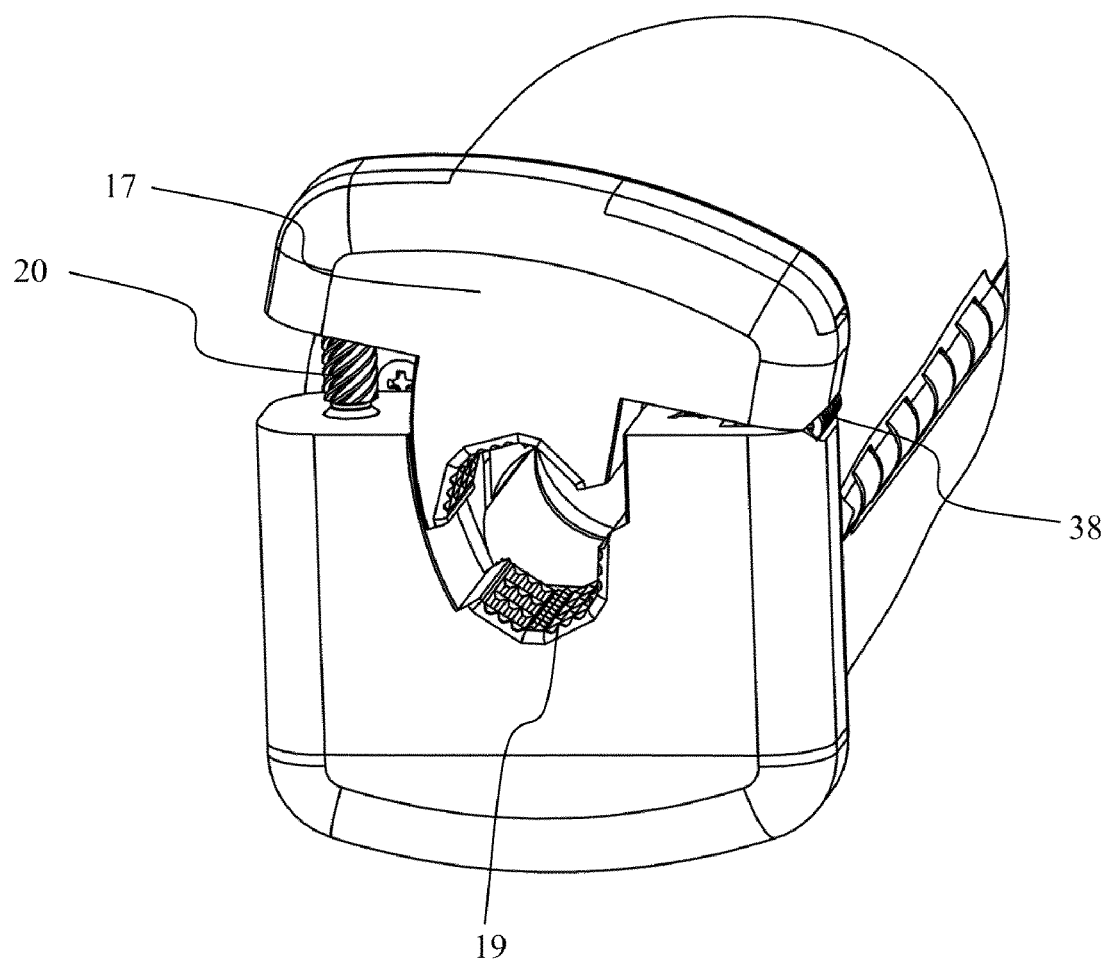
FIG. 10 is another general view of the handgrip of the invention.

FIG. 10 offers another view of the colonoscope handgrip system. The screw 20 preferably has multiple thread starts and a large thread pitch so that the movable grip portion 17 is lifted quickly about the hinge 38 upon rotation of screw 20. The inner surface of the grip assembly 18 contains a pattern of raised features 19 that firmly grips colonoscope shaft 2 without damaging it. This pattern may be optionally made using a compressible material such as silicone for example.

Figure 11A:
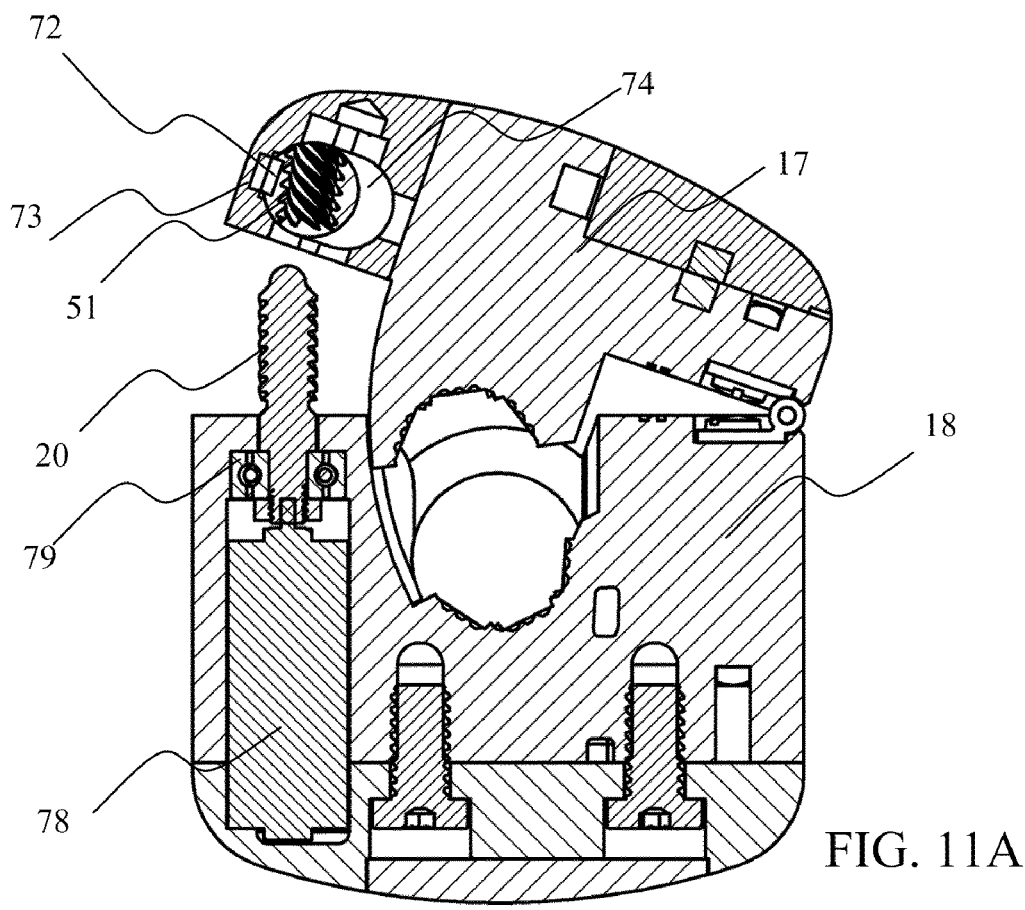
FIGS. 11A and 11B are the cross sections of the handgrip in respectively opened and closed positions.
Figure 11B:
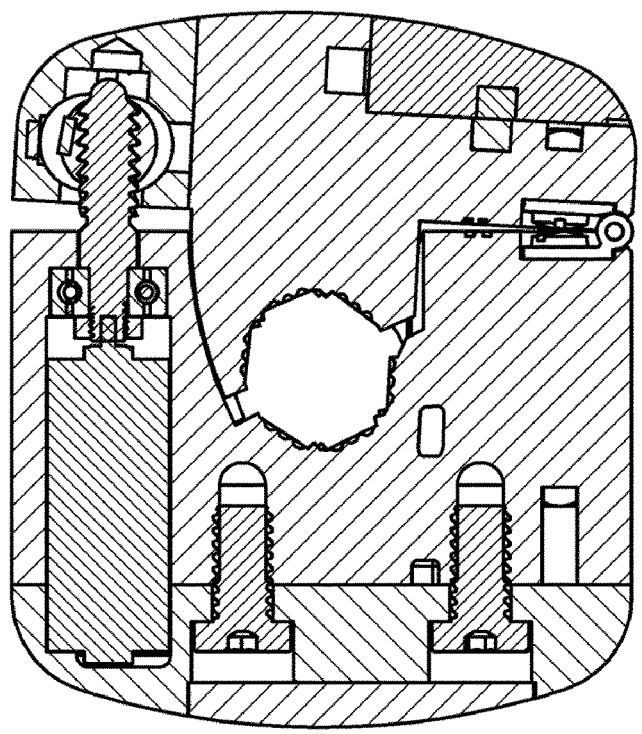

FIGS. 11A and 11B display a cross-sectional view of the colonoscope grip 18 in the open and closed position. The motor 78 is adapted to turn the screw 20 which is supported by a ball bearing 79. The nut 51 with the attached magnet 72 can be moved within the space 74. When the grip 18 is open, the nut 51 through the magnet 72 is attracted to the magnet 73. This allows the nut to be in the correct position for the grip to close. As the motor 78 turns the screw 20 in the opposite direction to close the grip 18, the nut 51 tilts its position within the space 54 to keep a proper alignment with the screw 20.

What is claimed is:

1. A handgrip for a colonoscope shaft comprising:
an internal sleeve adapted to be placed over and engaged with said colonoscope shaft,
an external sleeve slidingly positioned about the internal sleeve, and
an engaging means positioned between said internal and external sleeves, said engaging means further equipped with a force sensor, a torque sensor and an acceleration sensor, said force sensor adapted to measure force applied along said colonoscope shaft, said torque sensor adapted to measure rotational torque applied to said colonoscope shaft, and said acceleration sensor adapted to measure acceleration of motion of said handgrip.

2. The handgrip as in claim 1, wherein said acceleration sensor comprises a linear acceleration sensor adapted to measure linear acceleration along said colonoscope shaft and a rotational acceleration sensor adapted to measure acceleration of rotation applied to said colonoscope shaft.

3. The handgrip as in claim 1 further equipped with a wireless data transmission means.

4. The handgrip as in claim 1, wherein said acceleration sensor includes a 3-axis acceleration sensor, a 3-axis magnetometer, and a 3-axis gyroscope.

5. A handgrip system for measuring force, torque and motion acceleration applied to a shaft of a colonoscope, said system comprising:
a handgrip comprising in turn an internal sleeve adapted to be placed over and releasably engage with said colonoscope shaft, an external sleeve slidingly positioned about the internal sleeve, and an engaging means positioned therebetween and further equipped with a force sensor, a torque sensor, an acceleration sensor, and a data transmission means, and
an electronic unit for data receiving and processing.

6. The handgrip system as in claim 5, wherein said electronic unit further equipped with a display for presenting said force, torque, and acceleration data.

7. The handgrip system as in claim 6, wherein said acceleration sensor includes a 3-axis acceleration sensor, a 3-axis magnetometer, and a 3-axis gyroscope, said electronic unit is adapted to calculate said linear acceleration by measuring elevation, rotation, and azimuth angles of said handgrip relative to the gravity and magnetic vectors of the Earth; measuring 3-D acceleration vector by said 3-axis acceleration sensor; calculating 3-D acceleration vector produced by only displacement of said handgrip by subtracting of gravity vector from the 3-D acceleration vector; and calculating a projection of the 3-D acceleration vector to a central axis of said handgrip.

8. The handgrip system as in claim 7, wherein said electronic unit is further adapted to calculate rotational acceleration by measuring elevation, rotation and azimuth angles of said handgrip relative to the gravity vector of the Earth; measuring 3-D rotational accelerations by said 3-axis rotational gyroscope; and calculating the rotational acceleration about said colonoscope shaft from said 3-D rotational accelerations accounting for gravity vector of the Earth.

9. The handgrip system as in claim 5, wherein said electronic unit is adapted to compute a speed of handgrip motion and a change in positioning thereof, said computations based on data from said acceleration sensor.

10. The handgrip system as in claim 5, wherein said acceleration sensor includes a linear acceleration sensor to measure linear acceleration along said colonoscope shaft.

11. The handgrip system as in claim 5, wherein said acceleration sensor includes a rotation acceleration sensor to measure acceleration of rotation applied to said colonoscope shaft.

* * * * *